United States Patent [19]

Jarvik

[11] Patent Number: 4,863,461
[45] Date of Patent: Sep. 5, 1989

[54] ARTIFICIAL VENTRICLE

[75] Inventor: Robert Jarvik, Salt Lake City, Utah

[73] Assignee: Symbion, Inc., Salt Lake City, Utah

[21] Appl. No.: 170,982

[22] Filed: Mar. 21, 1988

[51] Int. Cl.$^4$ .............................................. A61F 2/22
[52] U.S. Cl. ....................................... 623/3; 623/900; 600/16; 600/17
[58] Field of Search ................... 623/3, 900; 128/1 D; 600/16, 17, 18, 36, 37

[56] References Cited

U.S. PATENT DOCUMENTS

| | | | |
|---|---|---|---|
| 3,568,214 | 3/1971 | Goldschmid | 623/3 |
| 4,173,796 | 11/1979 | Jarvik | 623/3 |
| 4,222,127 | 9/1980 | Donachy et al. | 623/3 |
| 4,369,530 | 1/1983 | Robinson et al. | 623/3 |
| 4,376,312 | 3/1983 | Robinson et al. | 623/3 |
| 4,381,567 | 5/1983 | Robinson et al. | 623/3 |
| 4,389,737 | 6/1983 | Robinson et al. | 623/3 |
| 4,453,537 | 6/1984 | Shitzer | 128/1 D |
| 4,662,358 | 5/1987 | Farrar et al. | 128/1 D |
| 4,704,120 | 11/1987 | Slonina | 623/3 |

OTHER PUBLICATIONS

The Total Artificial Heart by Robert K. Jarvik, Jan. 1981, Scientific American, vol. 24, no. 1, pp., 74–80.
Thrombus Generations Within the Artificial Heart by Oslen et al., Aug. 1975, The J. of Thoracic & Cardiovascular Surgery, vol. 70, No. 2, pp. 248–255.

Primary Examiner—Richard J. Apley
Assistant Examiner—Joe H. Cheng
Attorney, Agent, or Firm—Spensley Horn Jubas & Lubitz

[57] ABSTRACT

An artificial ventricle for replacing the human heart and comprising a shell formed from an upper housing and a lower base. A plurality of thin-walled, flexible pumping diaphragm layers are suspended from the base in a specific manner, and divide the shell into complementary upper and lower fluid receiving chambers. The diaphragm layers are shaped so as to travel through a specifically defined geometry of space. A seamless, thin-walled, Flexible blood bladder lines and occupies the upper chamber. The bladder has an upper portion attached to an inner surface of the housing, and an unadhered lower portion in contact with the pumping diaphragms.

26 Claims, 6 Drawing Sheets

ARTIFICIAL VENTRICLE

BACKGROUND OF THE INVENTION

1. Field of the Invention

In general, this invention pertains to medical prostheses, and in particular, to an artificial ventricle.

2. Description of the Related Art

Heart disease is presently the leading cause of death in the United States, claiming approximately a million lives each year. Responsively, both preventative and therapeutic measures have proliferated, the latter including the more extreme procedures of natural heart transplantation and artificial heart implantation.

As of this date, transplantation of human hearts has achieved an almost 80% short-term survival rate, due primarily to improvements in technique and antitissue-rejection drugs. However, a significant problem remains in that the number of potential transplant recipients far exceeds the number of donors available. This gap is one which portends well to be filled by mechanical or artificial hearts.

The concept of replacing the function of the heart with a mechanical pump is not new. In the later 1800's several attempts were made to develop designs for blood pump oxygenators, and in 1882, a simple, continuous-flow bubble oxygenator was demonstrated by Von Schroder.

A diaphragm pump intended to replace the function of both the right and left sides of the natural heart was devised by H. Dale and E. Schuster in 1928.

In 1934, M. DeBakey disclosed a simple roller pump which is presently used in all heart-lung machines.

In 1957, W. Kolff and T. Akutsu implanted two compact blood pumps made of polyvinyl chloride and powered by an extracorporeal compressed-air pump in a dog's chest to replace its heart.

In 1969, D. Cooley implanted a pneumatically-driven, total right and left ventricle prosthesis designed by D. Liotta in a human patient, who was kept alive by the prosthesis for 64 hours, at which time a donor heart was transplanted.

Beginning in about 1971, R. Jarvik and others at the University of Utah began development of a family of pneumatically-driven artificial hearts which culminated in 1976-1977 in a design referred to as the JARVIK-7, described in more detail hereinafter.

The JARVIK-7 has, to date, been implanted in more than 50 patients worldwide. When used as a permanent replacement for the patient's heart, this model has sustained patients for an average of nine months, but problems, including strokes and infection, have impaired the quality of life of the recipients.

However, if implanted temporarily in terminally-ill patients awaiting transplants, the model has shown to be capable of working satisfactorily to bridge the patient from almost certain death to satisfactory cardiac transplantation. As of today, 46 patients worldwide have been kept alive by the JARVIK-7 while awaiting transplantation. Thirty-four have survived long enough to receive new hearts. Of these, 26 are still alive.

One problem with prior devices is that of diaphragm durability. Tests have shown that the JARVIK-7, for example, can undergo about 200 million cycles without diaphragm failure, which results in a life of about 5 pumping years. It would be desirable to provide an artificial ventricle or heart having an expected life of between 7-10 years before need for replacement.

Another problem with existing devices is that of anatomical fit. It is desirable to provide an artificial heart having a shape which more closely duplicates the natural pericardial geometry.

Another problem with current devices is their high cost to produce. They are typically hand-made and rigorously hand-inspected for defects. Reject rates for clinical-grade devices may be high.

It is therefore an object of the present invention to provide an artificial ventricle which has a high diaphragm durability and reliability.

It is a further object of the present invention to provide a design which achieves a better anatomical fit than prior art devices.

It is yet a further object of the present invention to provide a design for an artificial ventricle which is consistent with high volume production techniques and which achieves a significant reduction in both manufacturing and quality assurance costs, thereby resulting in diminished unit costs.

It is still yet another object of the present invention to provide such an artificial ventricle as can be combined with a second, similar ventricle in a replacement for the human heart, and which can easily be scaled up or down in volume to obtain total artificial hearts (TAH's) for patients of all sizes.

SUMMARY OF THE INVENTION

These objects, and others, are achieved in an artificial ventricle having a resilient, thin-walled pumping diaphragm suspended within a semi-rigid, outer shell. The shell has a shape which is selected so as to achieve better anatomical fit. More specifically, the shell has a generally flattened oval shape with a race track-like longitudinal cross-section. The shell is comprised of an upper housing part and a lower base part, joined together by means of a specifically configured gasket. The gasket is also used to suspend the pumping diaphragm within the shell. Preferably, the pumping diaphragm is constructed of a plurality of flexible pumping diaphragm segments attached to and suspended within the housing at margins extending into a vertical groove between the base and the gasket. The pumping diaphragm divides the volume in the shell into complementary, variable-volume, upper and lower fluid-receiving chambers.

A blood bladder or sac is solution-molded to fit into the upper chamber and is adhered on an upper interior surface of the upper housing. The bladder has an integral, unadhered bottom portion which rests against, and is supported generally throughout its extent by, the pumping diaphragm. The bladder is molded to include a pair of radiused folds or pleats between the adhered upper portion and the unadhered lower portion, the outer one of which is supported laterally by, but is unadhered to, a radiused fillet located at the upper periphery of the gasket tangential to the housing at their intersection.

The upper chamber and blood sac communicate to the vestiges of a patient's right or left atria in order to inlet blood therefrom during ventrical intake, or diastole. A connector is provided which includes valve means for preventing backflow from the upper chamber and blood sac to the atria.

A second connector communicates the upper chamber and blood sac to either the patient's aorta (as in the case of a left ventricle), or pulmonary artery (as in the case of a right ventricle), for output, or systole, and is similarly provided with valve means for preventing backflow from the vessel into the ventricle.

A pressurized fluid, such as compressed air, is pumped into and out of the lower chamber between the base and a perforated insert located between the diaphragm and the base part. This pumping action causes the pumping diaphragm to distend contiguously upwardly into the upper chamber for systole, and contract downwardly into the lower chamber for diastole.

A better understanding of the artificial ventricle of the present invention, along with its many attendant objects and advantages, may be obtained from a consideration of the following detailed description of the preferred embodiments, particularly when read in conjunction with the appended drawings, a brief description of which now follows:

DESCRIPTION OF THE PREFERRED EMBODIMENTS

Figure 1:
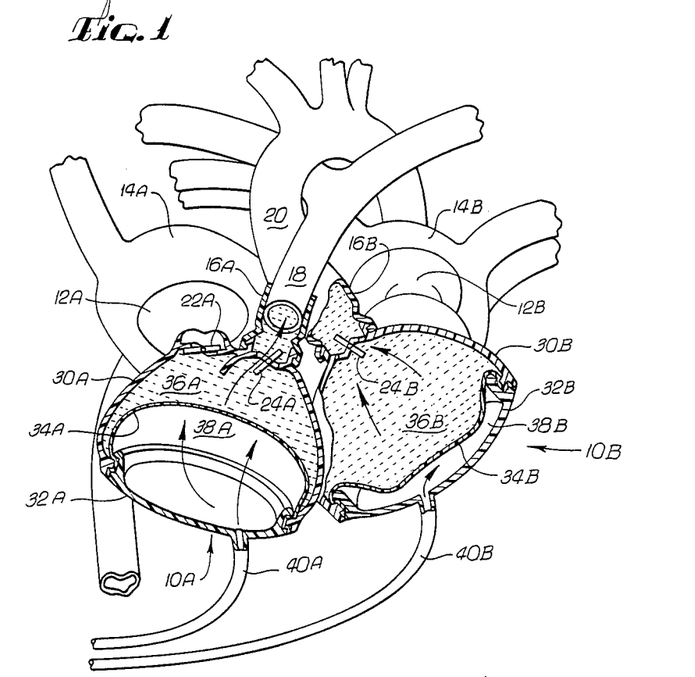
FIG. 1 is an anterior view of a pair of artificial ventricles implanted in the cardiopulmonary circulatory system of a human patient.

Illustrated in cross-section at FIG. 1 are a pair of artificial ventricles 10A and 10B of a prior art design shown interconnected with the major cardiopulmonary vessels of a human patient. An artificial right ventricle 10A is connected on an intake side by a connector 12A to the vestiges of the patient's right atrium 14A, and on its outlet side, is connected by means of a connector 16A to the patient's pulmonary artery 18. In a similar fashion, a left artificial ventricle 10B is interconnected on its inlet side by inlet connector 12B to the vestiges of the patient's left atrium 14B, and on its outlet side by an outlet connector 16B connected to the patient's aorta 20.

Each inlet connector 12A and 12B is provided with a one-way check valve, only the valve 22A provided for right ventricle 10A being shown, the other check valve not being visible in the view of FIG. 1. Each check valve is constructed to open to permit inflow of blood to the associated ventricle during diastole, i.e., ventricle intake, and to shut to prevent backflow from the associated ventricle to the atrium 14A or 14B during systole, i.e., the ventricle's pumping stroke.

Similarly, outlet connectors 16A and 16B are provided with one-way check valves 24A and 24B, respectively, which open during systole to permit outflow of blood from the ventricles to the pulmonary artery 18 and aorta 20, respectively, and which shut during diastole, or intake, to prevent backflow into the ventricles from these major vessels.

Artificial right ventricle 10A includes a semirigid, closed outer shell comprising an upper housing portion 30A and a lower base portion 32A joined together at an overlapping, sealed seam. Suspended at a margin within the shell in a region near the seam is a pumping diaphragm 34A, which divides the volume of the shell into complementary, variable-volume, fluid-receiving upper and lower chambers 36A and 38A, respectively. The volumes of chambers 36A, 38A depend upon the position of diaphragm 34A. A flexible tube 40A connects lower chamber 38A with a source of pumping fluid, e.g., compressed air, which is alternately pumped into and exhausted from lower chamber 38A to achieve the pumping action of the ventricle.

Left ventricle 10B is constructed and operates similarly to right ventricle 10A.

In FIG. 1, right ventricle 10A is shown undergoing systole in which compressed air is introduced into lower chamber 38A through tube 40A, causing diaphragm 34A to distend upwardly into upper chamber 36A and forcing blood through outlet connector 16A and check valve 24A into pulmonary artery 18, in the direction of the arrow shown. Operation of left ventricle 10B is similar and usually simultaneous. However, left ventricle 10B is shown at an earlier point in the systole phase.

During diastole, the procedure is reversed, with air being withdrawn from the lower chambers and blood being taken into the upper chambers from the atria through the inlet connectors.

From the above and by referring to FIG. 1, one can see that an artificial ventricle operates in many respects like an air-driven, diaphragm-actuated pump.

Figure 2:
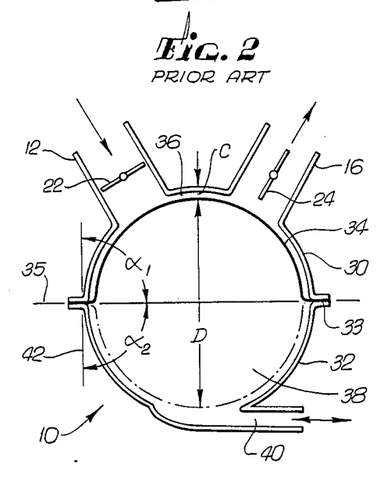
FIG. 2 is a generalized schematic representation of an artificial ventricle of the prior art.

FIG. 2 is a schematic cross-sectional view of the side of a generalized prior art artificial ventricle 10 which is illustrative of certain problems experienced by these devices. In FIG. 2, a semi-rigid spherical outer shell is comprised of an upper housing part 30 joined to a lower base part 32. A circular seam 33 is formed and a flexible diaphragm 34 is joined to the shell 10 adjacent seam 33. Diaphragm 34 divides shell 10 into complementary, variable-volume fluid-receiving upper and lower chambers 36 and 38, respectively. The movement of diaphragm 34 is illustrated in FIG. 2 by the solid line in its end-systolic position, and by the dotted line in its end-diastolic position. Although the prior art ventricle of FIG. 2 is illustrated as being generally spherical in shape, other similar configurations such as ellipsoidal have also been used.

Diaphragm 34 is typically attached by suspending it within the shell 10 at a circular margin attached to the shell in a region near seam 33. Between end-systolic and end-diastolic positions, the center of diaphragm 34 undergoes a total excursion indicated as D in the FIG.

Figure 3:
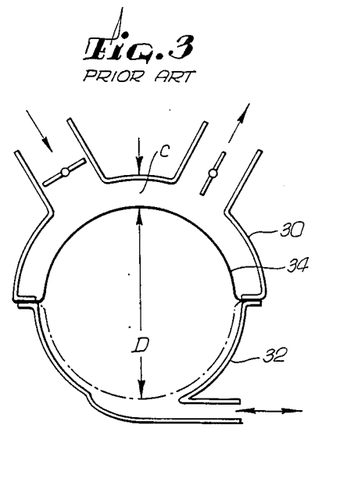
FIG. 3 is another generalized schematic representation of a prior art ventricle.

One of the problems with versions of such a device was the very small "headspace" C afforded between upper housing 30 and diaphragm 34 at end-systole. Thus, particularly when diaphragm 34 became stretched during extended use, the blood in upper chamber 36 could become "crushed" between the diaphragm and the housing, resulting in hemolysis, a very undesirable effect. This problem has been alleviated in the JARVIK-7 by sizing upper housing 30 to provide a larger headspace C between housing 30 and diaphragm 34, as illustrated schematically in FIG. 3. It is preferable that headspace C be not less than 0.150''–0.0200'' at the end-systolic position of diaphragm 34.

Figure 4:
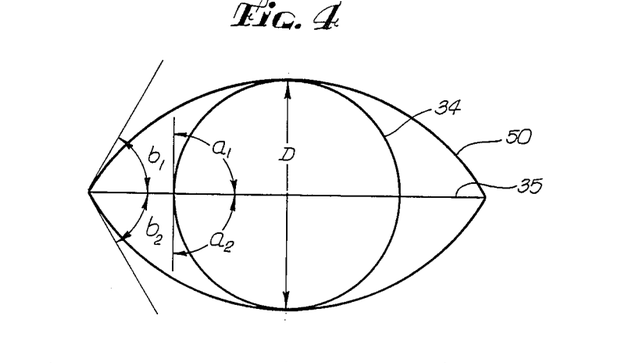
FIG. 4 is a geometric schematic illustrating diaphragm shapes.

Another problem experienced by prior art devices is that of the flexural stresses induced in the diaphragm in flexing between end-systole and end-diastole. Referring to FIG. 4, skilled practitioners will recognize that, regardless of the manner of attachment of the diaphragm to the shell, and regardless of whether the shell is ellipsoidal or spherical in shape, diaphragm 34 will undergo a maximum angular deflection at its point of attachment to the shell of $a_1 + a_2 = 180°$ between end-systolic and end-diastolic positions (where $a_1$ and $a_2$ each equals the angle between a tangent to the shell at the point of attachment and a diameter of the shell passing through the point of attachment, and $a_1 = a_2 \simeq 90°$). It has been discovered that this high degree of flexure at the point of attachment of the diaphragm is a source of fatigue and wear, and represents one limiting factor on the pumping life of the ventricle.

A partial solution to this problem is illustrated in the geometric schematic of FIG. 4. Here, the path traveled by a spherical or ellipsoidal diaphragm 34 is represented by a circle centered on a horizontal plane 35. The center of diaphragm 34 undergoes an excursion or "stroke length" of D between end-systolic and end-diastolic positions. If a segment of a larger ellipsoidal diaphragm 50 is superimposed upon diaphragm 34 such that its defining chord is coplanar with the horizontal plane 35 and the segment 50 is reflected about its defining chord, a more desirable diaphragm shape results. This may be visualized by taking a vertical "slice" through the diaphragms, as illustrated in FIG. 4. It will be noted that, regardless of where the slice is taken, the corresponding cut from the larger diaphragm will undergo a proportionately smaller deflection than a cut from the smaller diaphragm. In particular, for equal diaphragm center deflections D, spheroidal-segment diaphragm 50 will undergo a proportionately-smaller maximum angular deflection, which occurs at the region of its attachment, of $b_1 + b_2 < a_1 + a_2$, when compared to the spherical or ellipsoidal prior art diaphragm 34.

The benefits associated with this "flattened" diaphragm configuration also results in a more oblate (or flattened) configuration of the overall ventricle. This configuration for the overall ventricle has benefits in terms of anatomical fit, as described below.

It has been shown experimentally that if the overall angular deflection of the diaphragm is controlled such that the maximum angular deflection $b_1 + b_2 < 180°$, a significantly longer diaphragm life can be achieved. In particular, it is preferable to limit maximum diaphragm angular deflection to $b_1 + b_2 \leq 150°$, where $b_1 = b_2 = 70°$ to 75°.

Figure 5:
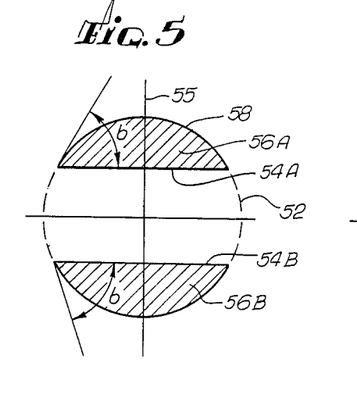
FIG. 5 is a cross-sectional geometric schematic of a sphere cut by a pair of parallel planes.
Figure 6:
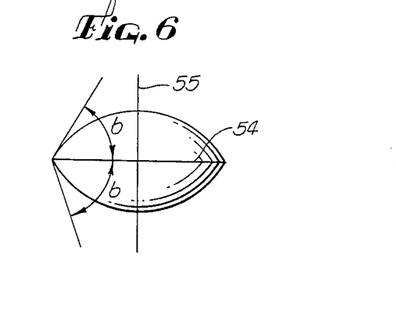
FIG. 6 is a geometric schematic of the spherical section of FIG. 5 with the subtended segments assembled together at a common chordal plane.

This concept is developed more fully at FIG. 5, where, in the cross-section of a sphere, circle 52 is cut by a pair of parallel chords 54A and 54B equally spaced on opposite sides of the circle's center to define a pair of circular segments 56A and 56B, and where the angle between the chords and a tangent to the circle at their intersection with the circle $= b < 90°$, or $\simeq 75°$. If segments 56A and 56B are "reassembled" at a common chord 54 and rotated through 180° about a diameter 55 of the circle perpendicular to the common chord, a surface having the shape illustrated in FIG. 6 results. This shape may be referred to as a right, oblate (flattened) spheroid, wherein the total angle between the surfaces of segments 56A, 56B at their intersection is $< 180°$, and preferably, between about 70° and 150°. This shape reflects the volume through which a diaphragm of the present invention travels.

Figure 7:
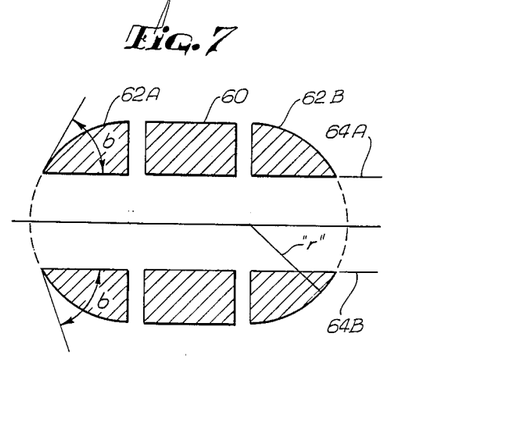
FIG. 7 is a schematic representation of a short cylindrical mid-section capped at both ends by a hemisphere and cut by a pair of parallel planes.
Figure 8:
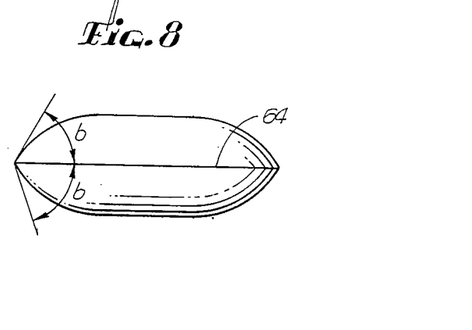
FIG. 8 is a geometric schematic of the spherical and cylindrical segments of FIG. 7 assembled together at a common chordal plane.

It has been found desirable to increase the volumetric capacity of the ventricle without increasing the radius. This may be accomplished by "stretching" the configuration illustrated in FIG. 6 to include an elongated center section, as illustrated generally at FIG. 7. Skilled practitioners will recognize the shape illustrated as that of a pressure vessel consisting of a short cylindrical mid-section 60 capped at either end by hemispheres 62A and 62B, having a radius "r". This vessel can be cut by a pair of parallel planes 64A and 64B equally spaced on and parallel to either side of the vessel's long central axis such that the planes intersect the surface at an angle of $b < 90°$ and $\simeq 70°$. The length of section 60 can be varied according to the desired pumping volume. Preferably, it is from about $\frac{1}{4}$ r to about r. When the pair of upper and lower sections thus formed are "reassembled" about a common plane 64, the resultant configuration is illustrated in FIG. 8. This shape represents the volume (i.e., the space) through which a preferred diaphragm of the present invention travels, and may be referred to as a right, oblate ovaloid. Because cylindrical and spherical geometries are used, the elongated diaphragm of the present invention can be made with the necessary precision and pressure requirements. More specifically, this overall shape lends itself well to numerically-controlled machining, as in the fabrication of molding tools for the diaphragms and shell parts.

The shape of the upper and lower inner surfaces of the ventricle shell of the present invention is configured such that the diaphragm can readily travel through the right, oblate ovaloid space discussed above. Thus, to a certain extent, the inner surface of the shell also has a configuration similar to the geometry of the path travelled by the diaphragm.

The diaphragm is attached to an inside surface of the shell such that it undergoes a maximum deflection of significantly less than 180°, and preferably, about 140° at its point of attachment. This results in a significantly reduced flexural stress in the diaphragm at its point of attachment. This stress is also uniform throughout the extent of the diaphragm's attachment, in distinction to prior art diaphragms.

Figure 9:
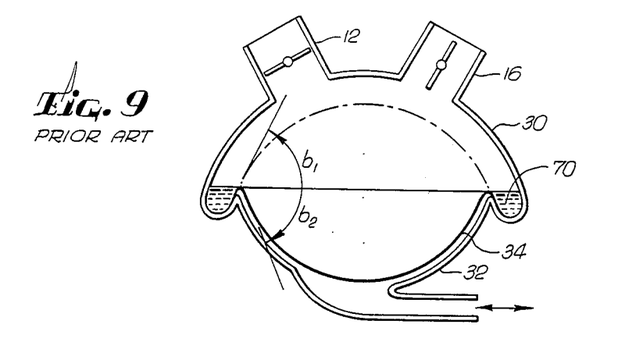
FIG. 9 is another generalized schematic representation of a prior art ventricle.

While FIGS. 5–8 are schematic illustrations of the path of travel of the diaphragm and inside of the shell of the present invention, the overlapping configuration illustrated in FIG. 9 is to be avoided. In FIG. 9, a pair of hemispherical or hemi-ellipsoidal housing segments 30 and 32 have diameters which "overlap" at the diaphragm-attachment boundary 37. In particular, if upper housing 30 is configured with a diameter or minor axis larger than that of the base, the region of overlap 37 can define a toroidal-shaped region of stasis 70 (shown cross-hatched in FIG. 9), a source of thrombogenesis. Generally, any site within the device which is conducive to stasis of the blood may be related to the formation of thrombi and is to be avoided. This includes not only regions of stasis of the type illustrated in FIG. 9, but any seam or boundary between dissimilar materials, as well.

Another problem associated with prior art devices involved the means used to form and attach the diaphragm bladder or sac used to contact the blood. Early efforts to achieve a functionally seam-free device surface in contact with the blood, as well as one substantially uniform in material, involved the inclusion of a blood "sac" or bladder within the volume of the ventricle. If at least a portion of the surface of the sac were free to move, and a pumping fluid, such as compressed air, were cyclically injected and exhausted into and from the region between the moveable portion and the ventricle's shell, a functioning pump could be achieved which had a seam-free surface of uniform material in contact with the blood pump. Earlier models involved dip-molding a bladder or sac from a resilient material, stretching and peeling the sac from around the mold or melting out the mold, and bonding the sac at some point to the inside of the ventricle housing. A version of this design is called the "Tethered Sack", and was developed by Dr. William Pierce. One of the problems associated with ventricles of this design is the difficulty encountered in attaching the bladder to the interior surface of the ventricle housing, wherein uniform adherence between the sac and the housing is difficult to achieve.

A procedure for molding the bladder within the housing by "solution-casting" it in place was developed at the University of Utah. In this procedure for bladder molding, an upper housing part is mated with a mold having a concave interior surface conforming to the ventricle's base part. In a procedure analogous to centrifugal-casting, uncured liquid bladder material is poured into the resulting hollow mold and allowed to form an internal "skin" contiguous with the housing. The excess material is then poured out of the assembly which is placed in a vacuum oven for drying and the mold part is then removed from the housing part. The result is an upper housing part having the upper surface of the bladder lining and integrally molded to its interior surface, with a lower portion of the bladder free to contract and expand in the manner of a "blood diaphragm" when the upper housing and bladder are subsequently mated with the lower base part of the ventricle. This methodology goes a fair way toward providing a functionally seam-free surface of uniform material in contact with the blood pumped by an artificial ventricle. A similar methodology is used in the present invention as discussed in detail below.

Another significant problem affecting artificial ventricle diaphragm longevity is related to the pumping diaphragm construction and manner of attachment and interaction with the housing. Early experiments have demonstrated that a diaphragm having a thickness sufficient to avoid stretching and "topping out" against the underside of the upper housing at end-systole would fail in short order due to the internal bending stresses induced by repeated flexure of the thicker section. The same is true for diaphgrams reinforced with, e.g., a Dacron mesh, due primarily to the interaction between the mesh and the material of the diaphragm.

Subsequent experiments have shown that it is preferable to have a plurality of thin-walled, flexible diaphragm segments which are lubricated interstitially with a lubricating material, preferably powdered graphite. The foregoing is equally true for a ventricle including an integrally-molded blood sac or bladder.

Accordingly, the ventricle of the present invention incorporates a relatively thin "blood diaphragm" integral with a solution-molded blood sac, as well as a separate and distinct "pumping diaphragm" in supporting contact with the blood diaphragm and disposed between the blood diaphragm and the source of pumping fluid. In one preferred embodiment, three thin-walled, flexible intermediate diaphragms are used between the pumping diaphragm and the blood diaphragm, the interstices between all of which are lubricated with powdered graphite.

The method of attachment of the diaphragms to the housing for flexure is also an important factor affecting diaphragm pumping life. In the case of the pumping diaphragm, it has been found that it can be simply "hung" or suspended by bonding it at its margins to a vertical, outer periphery of the base part such that, in its end-diastolic position, it is substantially supported throughout by the base. The diaphragm thus assumes a loose, draping "fold" or pleat in the region of its intersection with the base part, the latter being locally relieved and smoothly radiused to avoid stretching or kinking of the diaphragm at its point of suspension.

The method of attachment of the blood diaphragm to the housing is also important in terms of diaphragm longevity. In particular, it has been found that blood diaphragm longevity can be enhanced considerably by molding the blood diaphragm to incorporate a pair of adjacent, reversing "quarter-round" sections or folds immediately adjacent the line of attachment of the bladder or sac to the ventricle's housing, as in the case of a bellows. In this manner when the blood diaphragm is in the end-systolic position, the diaphragm achieves a full 180° radius extending tangentially outward from the line of attachment, and in the end-diastolic position, defines a reversing fold approaching a 180° reversal in direction. This "rolling" pleat can achieve significantly-enhanced diaphragm pumping life, and is incorporated in the preferred embodiment of the present invention.

Figure 10:
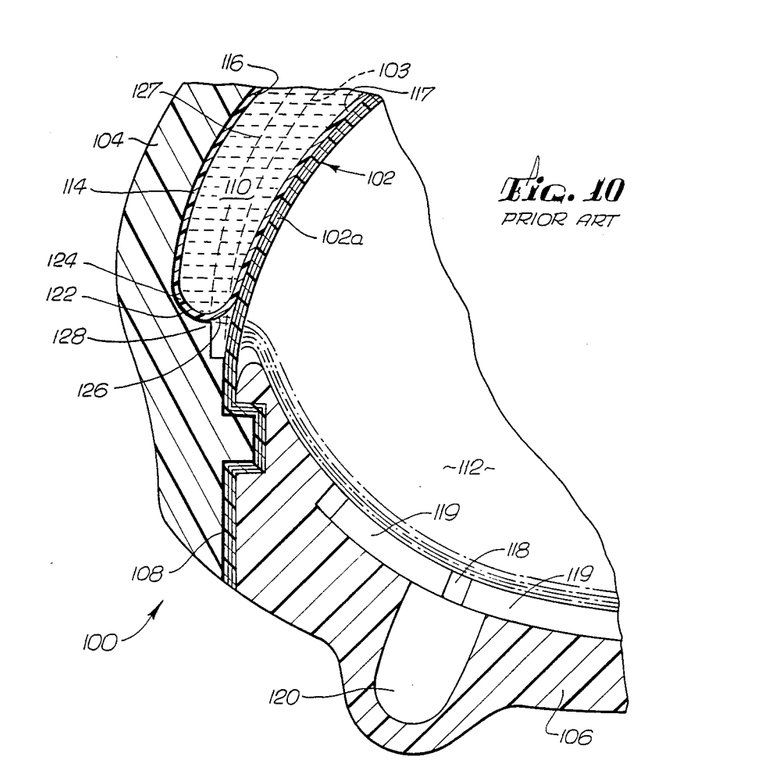
FIG. 10 is a detailed cross-section through the side of a JARVIK-7 ventricle.

The particular foregoing concepts can be more readily understood by reference to a prior art ventricle 100 illustrated in broken-away cross-section in FIG. 10. Artificial ventricle 100 is of a type known as the "JARVIK-7" and has been successfully implanted in human patients, as described hereinabove. Artificial ventricle 100 comprises a thin-walled, hemispherical pumping diaphragm 102. Diaphragm 102 is made of a plurality of thin-walled, flexible layers 102a which are bonded at a circular margin in seam 108 between an upper housing part 104 and a lower base part 106. Diaphragm 102 divides the housing into complementary upper and lower fluid-receiving chambers 110 and 112, respectively. The volume of chambers 110 and 112 is determined by the position of diaphragm 102 which, in FIG. 10, is illustrated by solid lines in an end-systolic position.

A thin-walled, resilient blood bladder or sac 114 occupies and lines the upper chamber 110. Blood sac 114 includes an upper portion 116 which is adhered substantially throughout its extent to an inside surface of housing part 104. This adherence is obtained by solution-casting a liquid, elastomeric material between upper housing 104 and a lower, concave mold (not illustrated) in the manner described hereinabove. The molding process additionally defines an unadhered portion in the form of a thin semispherical membrane or blood diaphragm 117 to be supported on its lower surface by an upper surface of diaphragm 102.

The interstitial spaces between blood diaphragm 117 and pumping diaphragm 102 are coated with a lubricating agent, i.e., graphite, to facilitate sliding of the surfaces relative to each other during systolic and diastolic movement of the membranes.

An opening 118 and a plurality of concentric and radial grooves 119 serve to communicate air or other pumping fluid conducted to base part 106 by conduit 120 with the underside of pumping diaphragm 102.

In FIG. 10, the end-diastolic position of diaphragm 102 and blood diaphragm 116 are illustrated in phantom lines. It will be noted that, in this position, the layers 102a of pumping diaphragm 102 are bonded in seam 108 to achieve a loose fold at the intersection of the seam and the base part 106. Base part 106 is provided with an ample radius in this region to clear the end-diastolic fold.

Upper housing 104 is formed to include a radiused cove or fillet 122 at the point at which blood diaphragm 117 departs adherence to its underside. Sac 114 is molded to incorporate consecutive, reversing, radiused bands or folds 124 and 126 in this region such that the first band 124 is adhered within cove 122 and the second band 126 is free to fold reversingly in a rolling motion between end-systolic and end-diastolic positions of blood diaphragm 117.

Extensive testing and clinical use of the JARVIK-7 have revealed areas wherein improvement can be realized relating to the ventricle's anatomical fit, manufacturability and diaphragm durability. These are the subject of the instant application.

Concerning anatomical fit, it will be noted that the JARVIK-7 ventricle is generally spherical in shape and, when joined with a similar ventricle to form a total artificial heart, results in an hour-glass shape. This design fits entirely to the left side of the midline in the patient's chest, with the left ventricle resting deeply within the chest and the right ventricle more anteriorly to its side. By flattening the ventricles to achieve the oblate ovaloid shapes discussed above, a pair of such ventricles joined together result in an overall volume having a flatter configuration, permitting the pair to be located more anteriorly in the limited space between the centrally-located atria and the sternum, i.e., more closely approximating the patient's natural pericardial geometry.

This new shape also enhances the durability of the diaphragms by limiting the maximum deflection of each diaphragm to <180° at its region of attachment, as well as constraining it to be uniform throughout that region. This results in a flexural stress in the region of attachment that is uniform and less than ventricles having either spheroidal or ellipsoidal shapes, as discussed above. In particular, extended durability tests have shown that the JARVIK-7, which is generally spherical in shape, can undergo about 200 million cycles before diaphragm failure, whereas a diaphragm constructed in accordance with the principles of the first or second preferred embodiment described herein may achieve upwards of 350 million cycles without failure, which results in a ventricle pumping life of better than seven years.

Another problem relating to diaphragm life of the JARVIK-7 ventricle is illustrated in FIG. 10, and relates to the method of attachment of the diaphragms. When they are new, the layers 102a of diaphragm 102 as well as blood diaphragm 117 assume the shape indicated by the solid lines at end-systole. However, over a period of time, the diaphragms, and in particular, diaphragm 102, will creep and become enlarged due to the air pressures it experiences at end-systole, and will assume the profile indicated by the broken line 103 in FIG. 10. This, in turn, distends blood diaphragm 117 in the same direction to the position shown by the broken line 127, resulting in a non-linear kink in the blood diaphragm along the juncture line 128 between blood diaphragm 117 and housing 104. It has been learned that this kinking problem in blood diaphragm 117 can be eliminated by insuring that the first, inwardly-radiused band 124 of the blood diaphragm is unadhered to housing 104 in the region of the supporting cove or radiused fillet 122, in a manner to be described hereafter.

Another problem relating to diaphragm durability in the JARVIK-7 ventricle, and in particular, pumping diaphragm 102, may be visualized in FIG. 10 at air hole 118 and circulation grooves 119 in the inner surface of base part 106. During end-diastole, air and intermediate diaphragms 102 are sucked against this surface, in order to ensure that no air bubbles are entrapped between air diaphragms 102 and base part 106. The lands between grooves 119 and the edge of air-hole 118 are extensive and relatively sharp, resulting in a non-linear stress being applied to the diaphragms at the sharp edges. Over time, this can lead to wear of these diaphragms. It has been learned that this problem can be greatly diminished by the provision of a pan-shaped insert between the base and the air diaphragms which has a concavity corresponding to the end-diastolic position of the diaphragms and a relatively large number of circular apertures whose diameter is small relative to the thickness of the air and intermediate diaphragms, as described in more detail hereafter.

Yet another problem with the JARVIK-7 ventricle illustrated in FIG. 10 relates to the assembly procedure of the ventricle. It may be recalled that the blood sac or bladder 114 is solution-molded within upper housing 104 and a hollow, lower concave mold. In order to accomplish registration between the housing and the mold, a registration tongue is molded into the housing, which tongue is subsequently cut away after assembly of the housing 104 to the base 106. Before this final assembly, pumping diaphragm segments 102a are bonded to base 106 consecutively and the assembly of the diaphragms and the base is then subsequently bonded into the housing and bladder assembly previously discussed along seam 108, as illustrated in FIG. 10. This final bonding operation must be carefully controlled by virtue of the lack of accurate means for registration of the base and air diaphragm assembly to the housing and bladder assembly, or its inspection after bonding.

Having defined these additional problems, their solution will now be addressed.

Figures 11, 12, 13, 14:
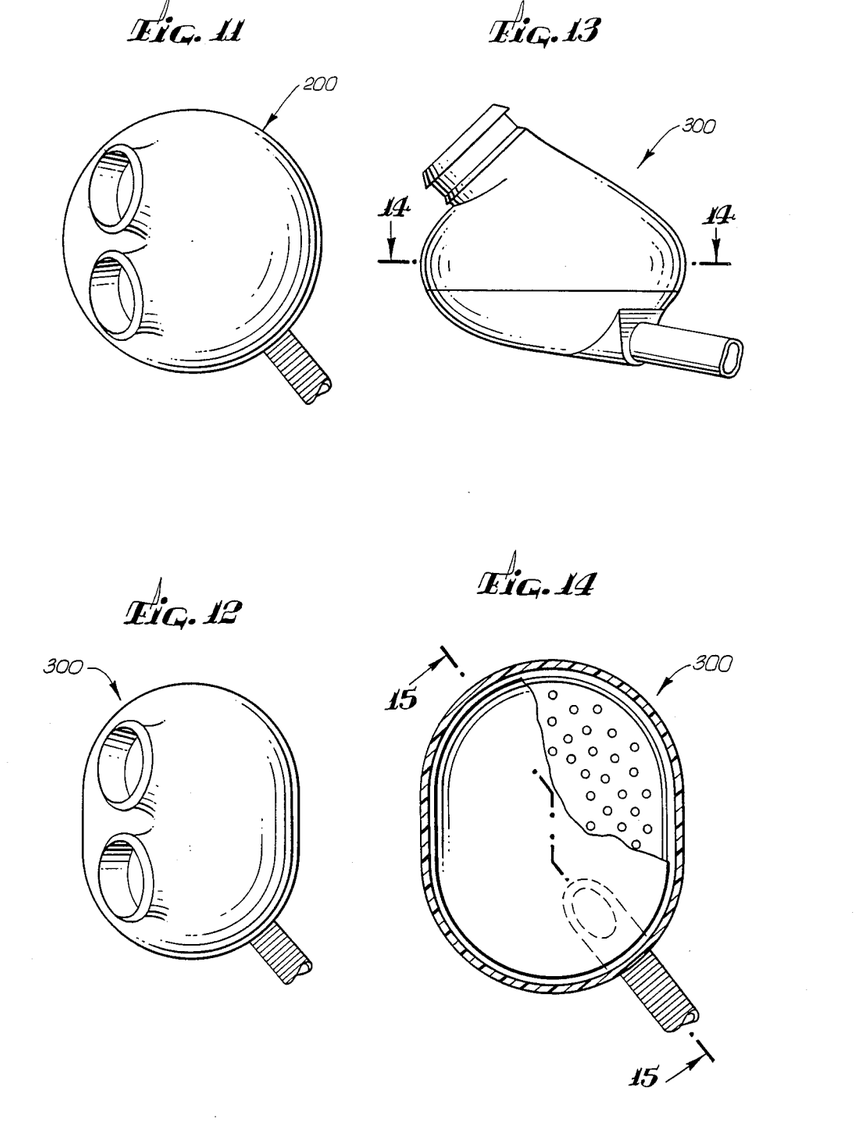
FIG. 11 is a plan view of an artificial ventricle in keeping with the present invention.
FIG. 12 is a plan view of a preferred embodiment of an artificial ventricle in keeping with the present invention.
FIG. 13 is an end view of the preferred embodiment of the ventricle, shown in FIG. 2.
FIG. 14 is a sectional view through the line 14—14 of FIG. 13.

Exemplary preferred embodiments of the outer shells of artificial ventricles of the present invention are illustrated in plan view in FIGS. 11 and 12. The difference between shells 200 and 300 is that, in the latter, an elongated center section is included. It will be noted that the use of a central section to achieve greater volume is likely. Accordingly, the detailed description of the preferred embodiment that follows is taken with reference to shell 300.

As illustrated in FIGS. 12, 13, 14 and 15, the ventricle comprises a semi-rigid shell 300 in the shape of a right oblate ovaloid. The shell 300 includes an upper housing portion 30 and a lower base portion 312. Portions 310, 312 intersect and are sealingly-connected to an outer gasket 314. A pumping diaphragm 316 is disposed between the housing 310 and base 312, and is preferably made of a plurality of thin-walled flexible pumping diaphragm layers 316a. Layers 316a are sealingly-bonded about their margins within an oval-shaped, vertically-extending groove 318 defined between outer gasket 314 and base part 312. The pumping diaphragm 316 divides the shell's internal volume into complementary, variable-volume upper and lower fluid-receiving chambers 320 and 322, respectively. In the sectional view of FIG. 15, pumping diaphragm layers 316a are shown in solid lines in their end-systolic positions, and in phantom lines in their end-diastolic positions. Pumping diaphragm layers 316a include at least one diaphragm layer in contact with a pumping fluid, e.g., compressed air, and a plurality of intermediate diaphragm layers, preferably three, which are lubricated between layers for relative sliding movement by a lubricating agent, e.g., powdered graphite. A blood sac or bladder 330 is solution-molded of an elastomeric material into upper chamber 320 in the procedure described hereinabove, such than an upper surface 332 is substantially adhered throughout its extent to an inner surface of upper housing 310. Bladder 330 has an integral unadhered bottom portion or blood diaphragm 334 which rests against, and is supported generally throughout its extent by, an upper pumping diaphragm layer 316a. Adjacent surfaces between blood diaphragm 334 and the uppermost pumping diaphragm layer 316a are also coated with a lubricant.

Figure 15:
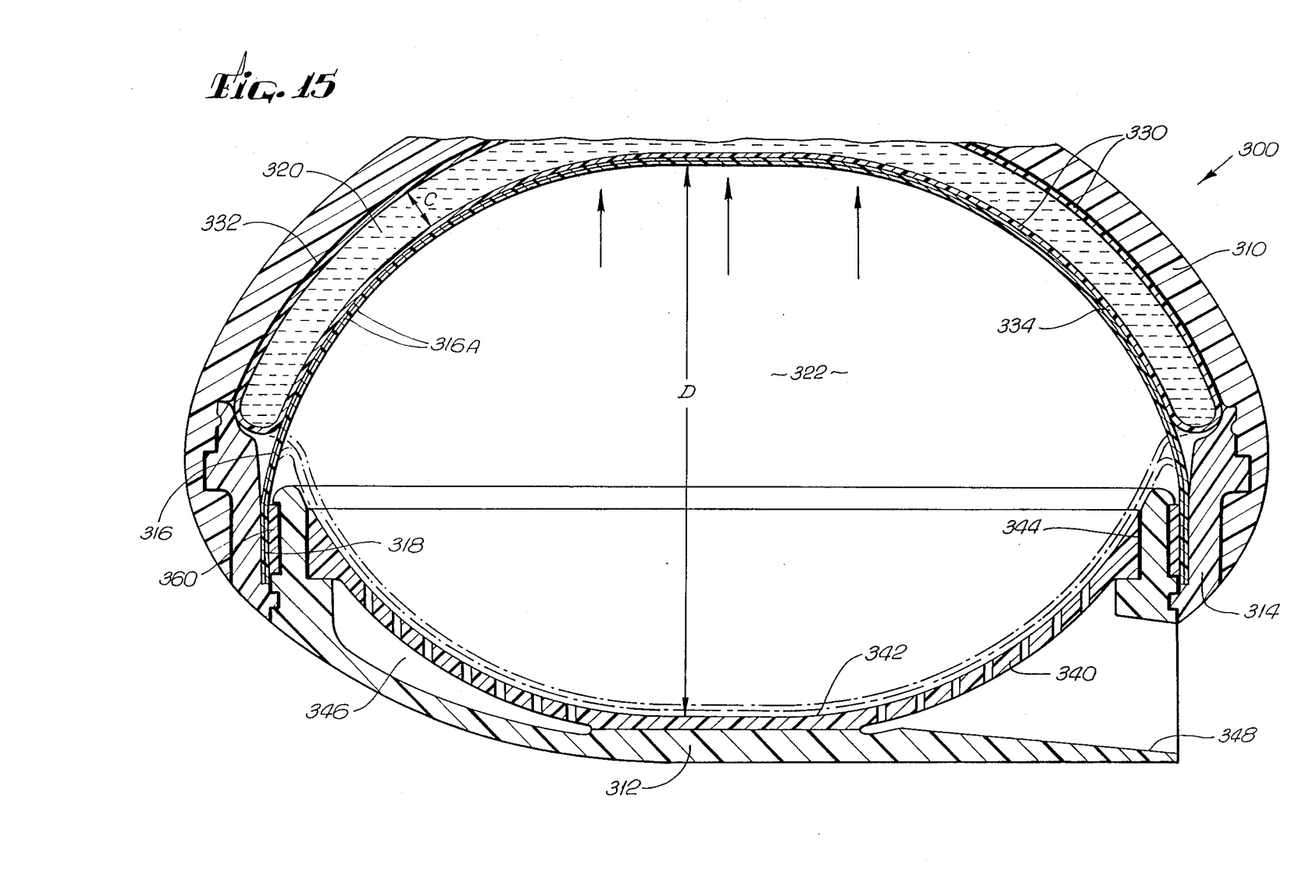
FIG. 15 is the sectional view through the section line 15—15 of FIG. 14.
Figures 16, 17:
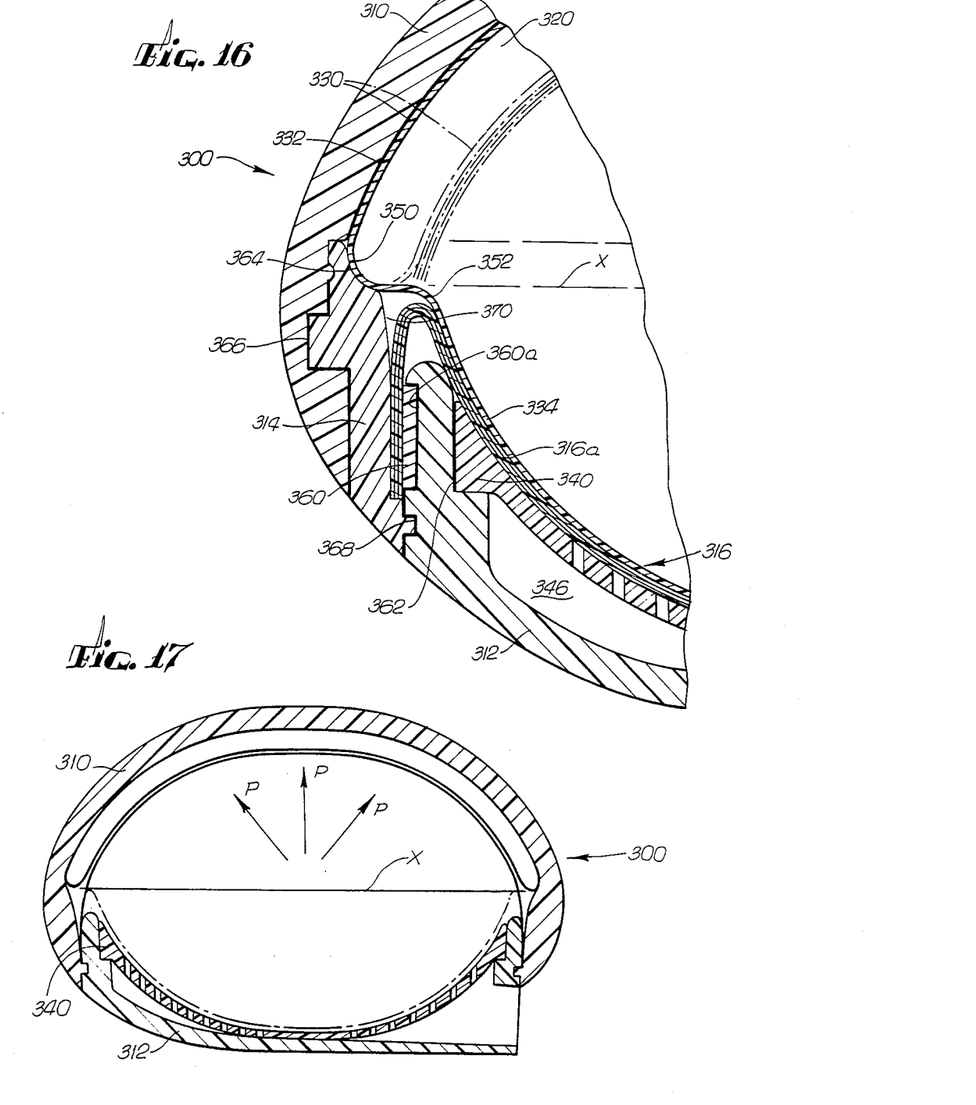
FIG. 16 is an enlarged sectional detail looking into the side of the preferred embodiment of FIG. 15.
FIG. 17 is a schematic view of the ventricle of the present invention illustrating an insert part and its effect on maintaining the configuration of the shell under pressure.

During a pumping cycle, pumping diaphragm 316 and blood diaphragm 334 move contiguously through the distance D between the end-systolic and end-diastolic positions illustrated in FIGS. 15 and 16. This configuration, in turn, results in a maximum diaphragm angular deflection at their regions of attachment of $<180°$, and preferably, $=140°$, between end-systolic and end-diastolic positions, for the reasons discussed above. The volume or space swept out by the travel of diaphragms 316, 334 is illustrated in FIGS. 7 and 8. That is, the volume is defined as having a short cylindrical mid-section capped at each end by hemispheres, and wherein the resulting configuration is cut by a pair of parallel planes parallel to the long axis, and the then-resulting sections joined together at the above-noted angle.

Upper housing 310 is conformed similarly to the diaphragms 316, 334 in their end-systolic position, and is spaced apart from blood diaphragm 334 at its end-systolic position by a headspace C which is preferably on the order of 0.150"–0.200".

Sandwiched between base part 312 and the diaphragms in their end-diastolic position is a pan-shaped insert 340. Insert 340 has an internal surface 342 having a shape generally conforming to that of the pumping diaphragm 316 in its end-diastolic position. Insert 340 is bonded to base part 312 at an outer periphery 344 and defines a volume 346 for receiving a pumping fluid, e.g., compressed air, between its underside and an inside surface of base part 312. The base part 312 also includes a molded-in bushing 348 for attachment of a tube to communicate the source of the pumping fluid to volume 346. Insert 340 includes a plurality of perforations whose diameter is significantly small relative to the thickness of the air diaphragms, and preferably, on the order of about 0.050", to communicate the pumping fluid to the lowermost of pumping diaphragm layers 316a. The configuration of insert 340 and its relationship to the way the diaphragm flexes up and down represents yet another important advance in the art. More specifically, the blood diaphragm 334 and the pumping diaphragm 316 flex about longitudinal axis X. (See FIG. 17.) Axis X lies on the plane which divides the shell 300 generally into two equal upper and lower volumes. As one can see from FIG. 17, insert 340 is located in base 312 such that as the diaphragms 316, 334 flex toward base 312, they are supported over their surface of contact by insert 340. Further, insert 340 and base 312 are relatively rigid. This permits the necessary pressures to be used, but without the bending and distorting of the semi-rigid shell and diaphragms associated with many prior art designs.

A better understanding of the fabrication of the diaphragms, and their method of attachment, may be obtained by reference to an enlarged detail section illustrated in FIG. 16. There, an injection-molded upper housing part 310 is mated with a mold (not illustrated) having a concavity corresponding with the shape of the blood diaphragm 334 in its end-diastolic position. The mold includes an inwardly-radiused cove or fillet subtending an arc of about 70° which is tangent to the housing's inner surface at their line of intersection. This mold fillet forms fold 350 of blood diaphragm 334. Located on the mold immediately adjacent to and tangent with this first fillet is a second "land" or inwardly-convex cove which is, at its innermost extremity, tangential to the surface of the blood diaphragm 334 in its end-diastolic position and which forms a fold 352.

The liquid blood sac material is poured into the volume within the housing and the mold and allowed to form a "skin" lining the entire volume; the uncured excess is then removed. When the mold is removed, the cured blood bladder 330 remains, with its upper surface 332 adhered to the underside of housing 310 and with a lower portion, comprising the blood diaphragm 334, conforming to the shape illustrated in FIG. 16. The shape includes, because of the configuration of the mold, the pair of contiguous, radiused folds or pleats 350 and 352, the latter of which is reversible in direction to the former such that, in an end-diastolic position, the angle between their extremities is about 140°, and in an end-systolic position, they are parallel.

Pumping diaphragm layers 316a are fabricated in an end-systolic position in a dip-molding procedure. In such procedure, a convex mold having the desired configuration is dipped into a solution of liquid diaphragm material to form a skin thereon of a desired thickness. The mold for the diaphragm layer in contact with the pumping fluid contains a peripheral groove, and an elastic registration band 360 is stretched over the mold and snapped into the groove before the mold is dipped. In this way, the resulting pumping diaphragm 316 has band 360 molded integrally into its margin. While this layer of diaphragm 316, "the air diaphragm," is still on the mold, the remaining intermediate pumping diaphragm layers are consecutively lubricated and layered over the first layer and bonded to it and each other at their margins, resulting in a pumping diaphragm assembly 316 which is easily inspected and having means for its accurate registration to the base 312.

Base 312 and insert 340 are both injected-molded from a relatively rigid plastic materal, e.g., a high durometer polyurethane. Before the pumping diaphragm assembly 316 is assembled to the base, insert 340 is bonded in a groove on the inside periphery of base 312 at the bond line 362 illustrated in FIG. 16. Base part 312 also includes an outer groove 360a conforming to the elastic registration band 360 previously bonded into the diaphragm assembly 316. The latter may now easily be slipped from the mold and accurately registered to base 312 for bonding after insertion of elastic band 360 into the registration groove 360a.

Outer gasket 314 is molded to incorporate an inwardly-radiused fillet or cove 364 which generally conforms in size and shape to the first radiused fold or pleat 350 of blood diaphragm 334 at its line of attachment to upper housing 310, and is tangential to the upper housing at that line. Outer gasket 314 is also molded to include a pair of registration features or tongues 366 and 368 to register it accurately to both housing part 310 and base part 312. Outer gasket 314 is first bonded to housing part 310, during which, care is taken to avoid any adhesive contact between blood diaphragm 334 and radiused fillet 364. The subassembly of the housing part 310, the bladder 330 and the outer gasket 314 are now ready to be mated with the subassembly of the base part 312, insert 340 and the diaphragm assembly 316 described above. This is accomplished by registration and bonding of registration tongue 368 on outer gasket 314 into the mating feature of housing 312, during which, the outer margin of diaphragm assembly 316 is bonded to an inner periphery of outer gasket 314. To avoid wicking adhesive material into the interstitial area between outer gasket 314 and the diaphragm surfaces during this procedure, outer gasket 314 is molded to include an outwardly-tapered portion 370 at its upper, inner periphery. Outer gasket 314 may also first be glued to the diaphragm base subassembly and subsequently glued into housing 310 in an alternative assembly sequence.

Skilled practitioners will recognize that the foregoing methods of manufacture and assembly lend themselves well to parts which are easily tooled for high-precision injection molding, dip-molding or solution molding, as well as to subassemblies which are easily inspectable for quality defects before final assembly.

After assembly, pumping diaphragm assembly 316 conforms to the shape shown by the solid lines in FIG. 16 in its end-diastolic position. Its center portion rests upon, and is supported by, insert 340. In the region of its attachment, base part 312 is both generously radiused and relieved away from the air gasket assembly 316 such that the latter contains a loose, draping fold in the region of its maximum flexure.

Similarly, blood diaphragam 334 is supported at the region of its attachment to upper housing part 310 by the radiused fillet 364 in outer gasket 314, and in its end-diastolic position, takes on the form shown in the solid lines in FIG. 16. However, since the first radiused portion 350 of the blood diaphragam is not adhered to the outer gasket in this region, it is free to separate and roll up away from the outer gasket in the event pumping diaphragm 316 stretches or becomes distended in its end-systolic position over an extended period of pumping. This manner of fabrication, attachment and support of the blood diaphragm essentially eliminates the kinking problem at its point of attachment previously described in connection with the JARVIK-7. Further, even if there should be some "creep" of the blood or pumping diaphragms, the necessary roll action of these members still goes on.

Similarly, practitioners will recognize that the configuration of the preferred embodiments is one having an added degree of flexibility in terms of overall ventricle size or stroke volume. For example, the embodiment illustrated in FIG. 11 is easily elongated into the embodiment illustrated in FIG. 12 to incororation additional stroke volume without increasing the ventricle's height or foregoing the enhanced durability of the diaphragms' configuration and method of attachment. Accordingly, a relatively wide range of ventricle outputs can be achieved in an anatomical fit more closely approximating that of the natural pericardial volume with molds which are easily and conventionally defined.

Indeed, skilled practitioners will by now recognize that many possible variations in terms of the materials, methods of manufacture and assembly discussed herein are possible, depending upon the particular problem at hand. Accordingly, the particular materials and the methods of fabrication and assembly discussed and illustrated herein should be taken as exemplary in nature, and the spirit and scope of the instant application limited only by the claims appended hereafter.

What is claimed is:

1. An artificial ventricle, comprising:
   a semi-rigid outer shell having a generally oval shape and comprised of an upper housing part, a lower base part, and means joining said parts together to form a sealed seam between said parts;
   blood pumping means including a thin walled, flexible diaphragm attached to said shell adjacent said seam and dividing said shell into sealed, complementary, upper and lower fluid receiving chambers, said diaphragm being movable between an end diastolic position wherein said diaphragm conforms to and is supported by said base part, and an end systolic position wherein said diaphragm conforms to and is spaced apart from said housing part by a predetermined head space, where said diaphragm is configured so that the end diastolic and end systolic positions of said diaphragm enclose a volume having the form of a right, oblate ovaloid which is symmetrical with respect to a median plane perpendicular to the direction of movement of said diaphragm between the end diastolic and end systolic positions, said ovaloid having, on each side of said median plane, two end sections each defined by a portion of a sphere and a midsection located between said end sections and defined by a portion of a cylinder, and wherein said end sections intersect said median plane such that, in a plane perpendicular to said median plane, the tangents to end sections which face one another on opposite sides of said median plane form an angle not greater than about 150°;
   means for directing blood into and out of said upper chamber; and means for connecting said lower chamber to a source of a pumping fluid, said pumping fluid selectively causing said diaphragm to move within said shell.

2. An artificial ventricle as defined in claim 1 wherein said outer shell has a generally oval outline in a plane parallel to said median plane.

3. An artificial ventricle as defined in claim 1 wherein said angle is about 140°.

4. An artificial ventricle as defined in claim 1 wherein said shell has a generally oblate ovaloid shape.

5. An artificial ventricle as defined in claim 1 wherein each spherical end portion has a radius r, and the length of the mid-section is from about ½ r to r.

6. An artificial ventricle as defined in claim 1 wherein the angle is from about 70° to 140°.

7. An artificial ventricle as defined in claim 1 wherein said blood pumping means further comprise:
a flexible bladder lining a portion of said upper chamber, said bladder including an upper portion which is adhered to said housing part and a lower portion which is integral with said upper portion, said lower portion defining a blood diaphragm.

8. An artificial ventricle as defined in claim 7, wherein said blood diaphragm has a pair of unadhered, contiguous, radiused pleats joined to said upper portion.

9. An artificial ventricle as defined in claim 8, wherein said means joining said housing parts comprise:
an outer gasket sealingly interconnecting said housing part to said base part, said gasket having an inner periphery defining an internal vertical groove between said gasket and said base part and containing an inwardly radiused cove, said cove seating and supporting one of said blood diaphragm pleats.

10. An artificial ventricle as defined in claim 1, further comprising:
an insert disposed between said base part and said diaphragm for seating and supporting said diaphragm when said diaphragm is in said end-diastolic position, said insert having a plurality of apertures therethrough communicating with said lower chamber.

11. An artificial ventricle, comprising:
a semi-rigid outer shell, including an upper housing part, a lower base part, and a sealing gasket sealingly interconnecting said housing part to said base part, said housing part and said base part being configured to define a sealed internal volume within said shell, said sealing gasket being formed to have a surface portion which is adjacent said housing part and faces toward said internal volume, said surface portion constituting a cove having a concave curvature, and said sealing gasket being formed to define, with said base part, an internal groove which comunicates with said internal volume;
a pumping diaphragm assembly having a plurality of thin walled, flexible, pumping diaphragm layers attached to said shell adjacent said groove and dividing said volume into sealed, upper and lower fluid-receiving chambers, said pumping diaphragm layers being collapsibly distensible between an end diastolic position where said pumping diaphragm layers conform to and are supported by said base part, and an end systolic position where said pumping diaphragm layers conform to and are spaced apart from said housing part by a predetermined head clearance;
a thin walled, flexible, blood bladder lining said upper chamber, said bladder having an upper portion with an upper surface adhered to said housing part adjacent said cove, and a lower portion which is integral with said upper portion, said lower portion defining a blood diaphragm which is distensible relative to said upper portion and which is movable with said pumping diaphragm layers in sliding contact with one of said pumping diaphragm layers, said blood diaphragm including a pair of unadhered, contiguous, radiused pleats adjacent said upper portion, one of said pleats lining said cove, and a second pleat having a curvature reversing in direction with movement of said blood diaphragm together with said pumping diaphragm layers between said end diastolic and end systolic positions;
means for directing blood into and out of said blood bladder; and
means for connecting said lower chamber to a source of a pumping fluid which selectively causes said pumping diaphragm assembly to move within said shell.

12. An artificial ventricle as defined in claim 11, wherein said gasket is tapered outwardly between said groove and said cove.

13. An artificial ventricle as defined in claim 11, further including a registration gasket located on one of said pumping diaphragm layers, and wherein said base part has a first slot located adjacent said groove, and said registration gasket is disposed in said first slot and registers said pumping diaphragm assembly with respect to said base part.

14. An artificial ventricle as defined in claim 13 wherein said housing part has a second slot and said sealing gasket extends into said second slot and thereby registers said housing part with respect to said base part.

15. A fluid pump adapted for use as an artificial ventricle, comprising:
a semi-rigid outer shell including an upper housing part, a lower base part, and means joining said parts together to form a sealed seam between said parts;
blood pumping means including a thin walled, flexible pumping diaphragm attached to said shell adjacent said seam and dividing said shell into sealed, complementary, upper and lower fluid receiving chambers, said diaphragm being movable between an end diastolic position wherein said diaphragm conforms to and is supported by said base part, and an end systolic position wherein said diaphragm conforms to and is spaced apart from said housing part by a predetermined head space, and wherein said diaphragm travels through upper and lower continuous volumes of space defined by:
taking a cylindrical midsection having a long axis perpendicular to the direction of movement of said diaphragm between said end diastolic and end systolic positions and being capped at each end with hemispherical end portions, cutting said capped cylindrical section into two substantially equal volumes of space by a pair of parallel planes parallel to said long axis, and then joining the two substantially equal volumes together;
means for directing blood into and out of said upper chamber; and
means for connecting said lower chamber to a source of a pumping fluid which selectively causes said diaphragm to move within said shell between said end diastolic and systolic positions.

16. A fluid pump as defined in claim 15 wherein said hemispherical end portions intersect said long axis and form, at the location of intersection with said axis, an angle no greater than about 150°.

17. A fluid pump as defined in claim 16 wherein said angle is about 140°, and further wherein said hemispherical end portions have a radius r, and the length of said midsection is from about ½ r to r.

18. A fluid pump as defined in claim 15, wherein said blood pumping means further comprise:
a flexible bladder lining a portion of said upper chamber, said bladder including an upper portion adhered to said housing part and a lower portion which is integral with said upper portion and which defines a blood diaphragm that is distensible relative to said upper portion.

19. A fluid pump as defined in claim 18, wherein said blood diaphragm has a pair of unadhered, contiguous, radiused pleats joined to said upper portion.

20. A fluid pump as defined in claim 19, wherein said means joining said parts together comprise:
an outer gasket sealingly interconnecting said housing part to said base part, said gasket having an inner periphery defining an internal groove between said gasket and said base part, said outer gasket being formed to have a surface portion which faces toward the interior of said shell and which constitutes a cove having a concave curvature, said cove seating and supporting one of said blood diaphragm pleats.

21. A fluid pump as defined in claim 15, further including a registration gasket disposed on said diaphragm, and wherein said base part defines a first slot located adjacent said seam, said registration gasket being disposed in said first slot thereby registering said diaphragm with respct to said base part.

22. A fluid pump as defined in claim 20, wherein said housing part defines a second slot and said outer gasket extends into said second slot thereby registering said housing part with respect to said base part.

23. A fluid pump adapted for use as an artificial ventricle, comprising:
a semi-rigid outer shell having a generally oval configuration and comprised of an upper housing part and a lower base part, said lower base part having first and second registration slots, and housing part being joined and registered with respect to said base part by means of said first registrations slot;
a thin walled, flexible pumping diaphragm attached to said shell and dividing said shell into sealed, complementary, upper and lower fluid receiving chambers, said diaphragm being movable between an end diastolic position wherein said diaphragm conforms to and is supported by said base part, and an end systolic position wherein said diaphragm conforms to and is spaced apart from said housing part by a predetermined head space;
means for directing blood into and out of said upper chamber;
means for connecting said lower chamber to a source of a pumping fluid which selectively causes said diaphragm to move within said shell;
a registration gasket joined to said diaphragm and disposed in said second registration slot, thereby registering said diaphragm with respect to said base part; and
a flexible bladder lining a portion of said upper chamber, said bladder including an upper portion which is adhered to said housing part and a lower portion which is integral with said upper portion and which defines a distensible blood diaphragm movable with said pumping diaphragm.

24. A fluid pump as defined in claim 23, wherein said blood diaphragm has a pair of unadhered, contiguous, radiused pleats joined to said upper portion.

25. A fluid pump as defined in claim 24, further comprising:
an outer gasket sealingly interconnecting said housing part to said base part, said outer gasket having an inner periphery defining an internal groove between said outer gasket and said base part, said outer gasket being formed to have a surface portion which faces toward the interior of said shell and which constitutes a cove having a concave curvature, said cove seating and supporting one of said blood diaphragm pleats.

26. A fluid pump adapted for use as an artificial ventricle, comprising:
a semi-rigid outer shell having a generally oval configuration and comprised of an upper housing part and a lower base part, said lower base part having first and second registration slots, and housing part being joined and registered with respect to said base part by means of said first registrations slot;
a thin walled, flexible pumping diaphragm attached to said shell and dividing said shell into sealed, complementary, upper and lower fluid receiving chambers, said diaphragm being movable between an end diastolic position wherein said diaphragm conforms to and is supported by said base part, and an end systolic position wherein said diaphragm conforms to and is spaced apart from said housing part by a predetermined head space;
means for directing blood into and out of said upper chamber;
means for connecting said lower chamber to a source of a pumping fluid which selectively causes said diaphragm to move within said shell;
a registration gasket joined to said diaphragm and disposed in said second registration slot, thereby registering said diaphragm with respect to said base part; and an insert disposed between said base part and said pumping diaphragm for seating and supporting said pumping diaphragm in said end diastolic position, said insert having a plurality of apertures therethrough communicating with said lower chamber.

* * * * *